United States Patent [19]

Konno et al.

[11] 4,075,121

[45] Feb. 21, 1978

[54] WOOD PRESERVATIVES AND METHOD FOR WOOD PRESERVATION TREATMENT

[75] Inventors: Kazuhiko Konno; Yosio Hayasi; Eiji Taniyama; Tetsuo Sekiya, all of Amimachi, Japan

[73] Assignee: Mitsubishi Petrochemical Company Limited, Tokyo, Japan

[21] Appl. No.: 662,084

[22] Filed: Feb. 27, 1976

[30] Foreign Application Priority Data

Mar. 3, 1976  Japan .................................. 51-25047

[51] Int. Cl.² ............................................ C09K 15/22
[52] U.S. Cl. .................................... 252/407; 252/403; 252/404; 252/405; 252/406
[58] Field of Search ............... 252/403, 404, 405, 406, 252/407; 21/7; 260/343.2 R, 343.5, 343.3

[56] References Cited

U.S. PATENT DOCUMENTS

| 3,634,289 | 1/1972 | Liddell | 252/404 |
|---|---|---|---|
| 3,723,465 | 3/1973 | Hall | 252/404 |
| 3,766,214 | 10/1973 | Lin et al. | 260/343.3 |
| 3,874,908 | 4/1975 | Liddell | 21/7 |
| 3,947,468 | 3/1976 | Hall | 252/404 |

*Primary Examiner*—Benjamin R. Padgett
*Assistant Examiner*—Josephine Lloyd
*Attorney, Agent, or Firm*—Wenderoth, Lind & Ponack

[57] ABSTRACT

A wood preservative composition for control of wood decay by fungi, which comprises 2H-benzopyran-2-spiro-3'-phthalide or its derivatives such as 6-methyl-2H-benzopyran-2-spiro-3'-phthalide or benzo[f]-2H-benzopyran-2-spiro-3'-phthalide as an active ingredient. The active ingredient has extremely low mammalian toxicity, and exhibits an excellent wood-decay controlling effect.

5 Claims, No Drawings

WOOD PRESERVATIVES AND METHOD FOR WOOD PRESERVATION TREATMENT

This invention relates to wood preservatives useful for protecting woods from decay, especially decay caused by the attack of wood-decaying microorganisms, and to a method for wood preservation treatment. More specifically, the invention relates to a wood preservative composition containing an active ingredient which has low toxicity to warm-blooded animals and can control the growth of wood-decaying microorganisms or combat these microorganisms growing on woods, and to a method for wood preservation treatment using the above active ingredient.

The active ingredient of the wood preservative composition of the invention is 2H-benzopyran-2-spiro-3'-phthalide or its derivatives expressed by the following formula

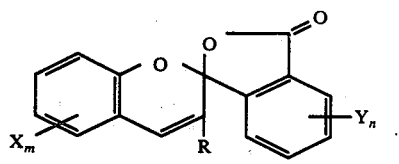

wherein each of X and Y is a member selected from the group consisting of halogen atoms, a nitro group, an amino group, alkyl groups, alkenyl groups, alkoxy groups, alkylthio groups and alkyl-substituted amino groups; $m$ and $n$ are an integer of 0 to 4, and when $m$ is an integer of 2 to 4 an $n$ is an integer of 2 to 4, a plurality of members X and Y may be identical or different; R is a member selected from the group consisting of a hydrogen atom, alkyl groups and a phenyl group; and each of X and Y may be positioned at two adjacent atoms on the benzene ring and may form another benzene ring together with these carbon atoms.

The active compound of formula (I) can be easily prepared, for example, by the process described in the paper by Sato et al. in COLLECTION OF PREPRINTS, 28TH SPRING CONFERENCE OF THE CHEMICAL SOCIETY OF JAPAN, page 1752, 1973. For example, in accordance with formula (a) in the following reaction scheme, acetophenone-O-carboxylicacid or its derivative (IV) is reacted with salicylaldehyde or its derivative (III) in the presence of an alkaline substance such as sodium hydroxide in a lower alcohol solvent such as ethanol, preferably at an elevated temperature thereby to form a 2'-carboxy-2-hydroxychalcone (II). A cyclization reaction of the chalcone (II) with an acid such as conc. sulfuric acid readily yields a compound of formula (I). Or in accordance with formula (b) in the following reaction scheme, the compound of formula (IV) and the compound of formula (III) are dissolved in conc. sulfuric acid and contacted with each other at room temperature to afford the compound of formula (I). Or the compound of formula (I) can be prepared in accordance with formula (c) in the following reaction scheme, by treating the compound of formula (IV) with acetyl chloride to form 3-methylene phthalide of formula (V) and then condensing this compound with the compound of formula (III) in sulfuric acid.

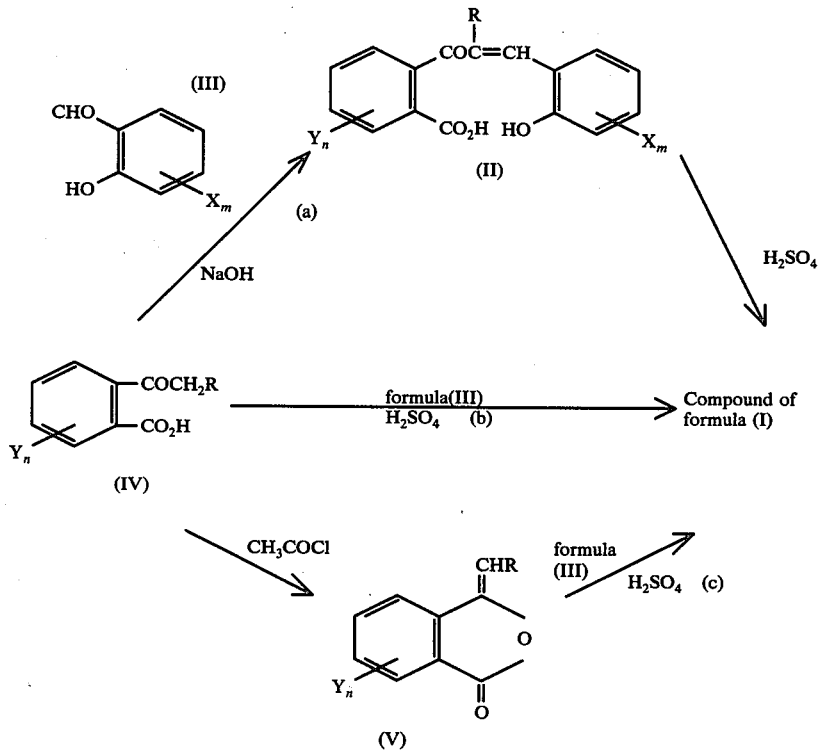

The excellent wood decay controlling effect of the compounds of formula (I) and their low toxicity to warm-blooded animals, especially mammals, have not been known heretofore.

It has been well know that the activities of various microorganisms which decompose wood components such as cellulose or lignin are associated with the deterioration or decay of woods. Because of the shortage of wood resources it has been strongly desired to protect wood from decay and inhibit wood deterioration by controlling the growth of such wood-decaying microorganisms in wood or combatting these microorganisms growing on wood.

Pentachlorophenol sodium salt or organotin compounds such as tributyltin oxide have previously been utilized for the preservation treatment of wood. Such wood preserving chemicals, however, have high toxicity to warm-blooded animals, especially mammals, and their use poses a serious problem. For example, in oral administration to mice, the pentachlorophenol sodium salt has an $LD_{50}$ of 92 mg/Kg of body weight, and the tributyltin oxide has an $LD_{50}$ of 175 mg/Kg of body weight. Furthermore, the latter gives off a peculiar offensive smell.

We made investigations in an attempt to develop superior wood preservatives free from the toxicity and other defects mentioned above, and a method for preservation treatment of wood using such wood preservatives. These investigations led to the discovery that the 2H-benzopyran-2-spiro-3'-phthalide or its derivatives of formula (I) which can be prepared easily on a commercial scale exhibit controlling effects against microorganisms that attack and decay woods, and have markedly low toxicity as shown by their $LD_{50}$ of 7600 mg/Kg of body weight in oral administration to mice.

Accordingly, it is an object of this invention to provide wood preservatives which exhibit excellent controlling effects aganist wood-decaying microorganisms.

Another object of this invention is to provide a method for preservation treatment of wood which exerts a superior effect against the decay of wood ascribable to the attack of wood-destroying microorganisms.

The above and other objects of this invention along with its advantages will become more apparent from the following description.

According to the present invention, the attack of microorganisms that cause decay of the wood in its broadest sense which is being, or to be, used in a variety of places such as outdoors, indoors, or building structures can be controlled significantly. The term "wood", as used in the present application, is meant to include unprocessed wood such as logs as felled or deprived of barks; primary wood products such as boards, bars, planks, blocks, tiles or the like which are utilized as wooden materials in a wide range of fields such as civil engineering, building, vehicle building, shipbuilding, furniture making, engraving, or decoration; and finished wood products containing wood cellulose such as plywood and particle board.

Preferred species of the compound of formula (I) are those of formula (I) wherein each of X and Y is a member selected from the group consisting of halogen atoms, a nitro group, an amino group, alkyl groups containing 1 to 4 carbon atoms, alkenyl groups containing 2 to 4 carbon atoms, alkoxy groups containing 1 to 12 carbon atoms, alkylthio groups containing 1 to 12 carbon atoms, and $C_1-C_6$ alkyl-substituted amino groups, R is a member selected from the group consisting of a hydrogen atom, alkyl groups containing 1 to 4 carbon atoms and a phenyl group, m and n are the same as defined hereinabove, and X and Y may respectively form another benzene ring as described hereinabove.

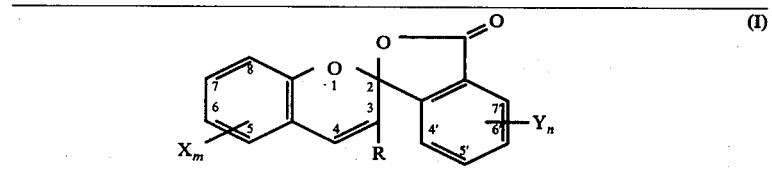

| No. | Compound | X | m | Y | n | R | Melting Point (° C) |
|---|---|---|---|---|---|---|---|
| 1 | 2H-Benzopyran-2-spiro-3'-phthalide | — | 0 | — | 0 | H | 113 – 114 |
| 2 | 6-Bromo-2H-benzopyran-2-spiro-3'-phthalide | Br | 1 | — | 0 | H | 196 – 196.5 |
| 3 | Benzo[f]-2H-benzopyran-2-spiro-3'-phthalide |  |  | — | 0 | H | 214 – 215 |
| 4 | 6-Nitro-2H-benzopyran-2-spiro-3'-phthalide | $NO_2$ | 1 | — | 0 | H | 208.5 – 210.5 |
| 5 | 6-Chloro-2H-benzopyran-2-spiro-3'-phthalide | Cl | 1 | — | 0 | H | 187 – 187.5 |
| 6 | 6-Methyl-2H-benzopyran-2-spiro-3'-phthalide | $CH_3$ | 1 | — | 0 | H | 195.5 |
| 7 | 8-Methoxy-2H-benzopyran-2-spiro-3'-phthalide | $OCH_3$ | 1 | — | 0 | H | 209 – 210.5 |
| 8 | 6-Methoxy-2H-benzopyran-2-spiro-3'-phthalide | $OCH_3$ | 1 | — | 0 | H | 202 – 203 |
| 9 | 6-Nitro-2H-benzopyran-2-spiro-3'-(4',5',6',7'-tetrachlorophthalide) | $NO_2$ | 1 | Cl | 4 | H | 236.5 – 237 |
| 10 | 7-N,N-Dimethyl-amino-2H-benzopyran-2-spiro-3'-(4',5',6',7'-tetrachlorophthalide) | $N(CH_3)_2$ | 1 | Cl | 4 | H | 235 (dec.) |
| 11 | 3-Methyl-2H-benzo- | — | 0 | — | 0 | $CH_3$ | 78 – | trates at least into the surface portion of the wood. Any desired means of ensuring full contact between the compound of formula (I) and the wood can be used, for example, coating, spraying, dipping, or injection. If desired, this contact treatment is carried out at an elevated temperature and/or an elevated pressure. The wood to be treated is in the form of not only unprocessed or processed woods, but also wood products such as building structures, furniture or shipbuilding structures.

The active compound of formula (I) used in this invention is applicable to all microorganisms which cause decay of woods, but it is especially effective against fungi of the Basidiomycetes group. Example of such fungi are as follows:

Coniophora cerebella,
Poria placenta,
Polystictus versicolor,
Lenzites abietina,
Trametes trabea,
Poria vaporaria
Paxillus pannoides,
Gloeophyllum trabeum,
Poria vaillantii,
Poria monticola,
Polystictus hirsutus,
Coniophora puteana,
Tyromyces palustris,
Lenzites gibbosa,
Lenzites betulina,
Coriolus versicolor,
Lenzites sepiaria,
Lenzites trabea,
Polystictus abietinus,
Schizophyllum commune,
Merulius lacrymans,
Polystictus sanguineus,
Lentinus lepideus, and
Polyporus insularia.

The following Examples and Test Examples illustrate the present invention in greater detail. The microorganisms used in these examples as wood-decaying fungi are microorganisms selected in JIS (Japanese Industrial Standards), ASTM (United States), and DIN (German Industrial Standards).

EXAMPLE 1 (oil-soluble preparation)

0.5 Part of compound No. 1 was dissolved in 5 parts of dimethyl sulfoxide, and 5 parts of methylnaphthalene and 89.5 parts of solvent naphtha were added to form an oil preparation. The oil preparation was used to treat wood by coating or dipping, etc.

EXAMPLE 2 (emulsifiable concentrate)

5 Parts of compound No. 6 was dissolved in 40 parts of dimethyl sulfoxide, and 50 parts of xylene and 5 parts of polyoxyethylene nonylphenyl ether were added. They were fully mixed to form an emulsifiable concentrate. The emulsifiable concentrate was diluted with water to a suitable concentration, and applied to wood by coating, dipping, etc.

Test Example 1

Antimicrobial test on wood-decaying fungi:

Each of the wood-decaying fungi shown in Table 1 was inoculated in an agar culture medium (2% malt extract, 0.5% peptone) containing each of the compounds shown in Table 1 in the concentrations indicated in Tables 1 and 2, and the growth of the fungi was observed after the periods indicated in Tables 1 and 2. The degree of fungus growth inhibition of each of the compounds was determined, and the results are shown in Tables 1 and 2.

$$\text{Degree of fungus growth inhibition} = \frac{c - c'}{c} \times 100$$

wherein
- $c$ is the diameter (mm) of the colony of the growing fungus on a culture medium containing no wood-preservative chemical, and
- $c'$ is the diameter (mm) of the colony of the growing fungus on a culture medium containing the wood-preservative chemicals in accordance with this invention.

Table 1

| Compound No. | Coriolus versicolor | | | | Tyromyces palustris | | | |
| | 72 hours later | | 96 hours later | | 72 hours later | | 96 hours later | |
| | 100 ppm | 50 ppm | 100 ppm | 50 ppm | 100 ppm | 50 ppm | 100 ppm | 50 ppm |
|---|---|---|---|---|---|---|---|---|
| 1 | 100 | 100 | 100 | 100 | 100 | 100 | 100 | 100 |
| 2 | 100 | 92 | 95 | 85 | 100 | 95 | 98 | 86 |
| 3 | 100 | 100 | 100 | 90 | 100 | 100 | 100 | 95 |
| 4 | 92 | | 83 | | 94 | | 87 | |
| 5 | 100 | 90 | 97 | 84 | 100 | 93 | 96 | 84 |
| 6 | 100 | 100 | 100 | 98 | 100 | 100 | 100 | 100 |
| 7 | 89 | | 80 | | 91 | | 88 | |
| 8 | 92 | | 81 | | 90 | | 79 | |
| 9 | 98 | | 84 | | 91 | | 87 | |
| 10 | 95 | | 82 | | 94 | | 85 | |
| 11 | 100 | 100 | 100 | 96 | 100 | 100 | 100 | 98 |
| 12 | 90 | | 85 | | 87 | | 81 | |
| 13 | 97 | | 84 | | 98 | | 86 | |
| 14 | 92 | | 80 | | 95 | | 82 | |
| Pentachlorophenol, Na salt | 100 | 100 | 100 | 100 | 100 | 100 | 100 | 100 |

-continued

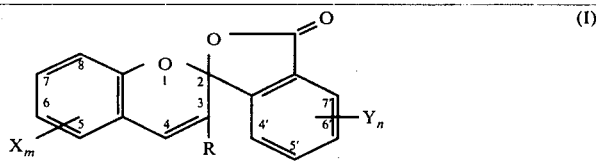

(I)

| No. | Compound | X | m | Y | n | R | Melting Point (° C) |
|---|---|---|---|---|---|---|---|
| | pyran-2-spiro-3'-phthalide | | | | | | 79 |
| 12 | 7-N,N-Dimethyl-amino-3-methyl-2H-benzopyran-2-spiro-3'-phthalide | N(CH$_3$)$_2$ | 1 | — | 0 | CH$_3$ | 189.5 |
| 13 | 6-Nitro-3-methyl-2H-benzopyran-2-spiro-3'-phthalide | NO$_2$ | 1 | — | 0 | CH$_3$ | 200 |
| 14 | 3-Phenyl-2H-benzopyran-2-spiro-3'-phthalide | — | 0 | — | 0 | phenyl | 147 – 148.5 |
| 15 | 8-Methylthio-2H-benzopyran-2-spiro-3'-phthalide | SCH$_3$ | 1 | — | 0 | H | — |
| 16 | 6-Vinyl-2H-benzopyran-2-spiro-3'-phthalide | —CH=CH$_2$ | 1 | — | 0 | H | — |
| 17 | 2H-Benzopyran 2-spiro-3'-benzo[f]-phthalide | — | 0 | (fused ring) | | H | — |
| 18 | 6-Methyl-8-methoxy-2H-benzopyran-2-spiro-3'-(4'-chlorophthalide) | { OCH$_3$, CH$_3$ } | 1, 1 | Cl | 1 | H | — |
| 19 | 6-iso-Butyl-2H-benzopyran-2-spiro-3'-phthalide | i-butyl | 1 | — | 0 | H | — |
| 20 | 6-Allyl-2H-benzopyran-2-spiro-3'-phthalide | allyl | 1 | — | 0 | H | — |
| 21 | 8-lauryloxy-2H-benzopyran-2-spiro-3'-phthalide | lauryloxy | 1 | — | 0 | H | — |
| 22 | 7-N,N-dihexylamino-2H-benzopyran-2-spiro-3'-phthalide | N,N-dihexyl-amino | 1 | — | 0 | H | — |
| 23 | 3-Butyl-2H-benzopyran-2-spiro-3'-phthalide | — | 0 | — | 0 | butyl | — |

The wood preservative composition of this invention comprises an amount effective to control wood decay of the compound of formula (I) and a diluent or carrier. The diluent or carrier may be a solid, liquid or gas, and examples include inert solid carriers such as clay, talc, bentonite, kaolin, silicic anhydride, calcium carbonate, methyl cellulose, carboxymethyl cellulose, a vinyl acetate resin, or sodium alginate; liquid carriers such as kerosine, ligroin, xylene, methylnaphthalene, solvent naphtha, dimethyl formamide, dimethyl sulfoxide, or propanesulfone; and gaseous carriers such as nitrogen gas, dimethyl ether, or fluorinated hydrocarbons. The wood preservative composition of this invention may also comprise other diluents or carriers having an action of facilitating the penetration or diffusion of the active ingredient of the composition into wood. Examples of such diluents or carriers include surface active agents such as cationic, anionic and nonionic surfactants.

The composition of this invention may be in various formulations according to the desired application, for example, an oil-soluble preparation, emulsifiable concentrate, paste, aerosol or wettable powder. It may also be in the form of a coating composition such as paint, lacquer or varnish for coating on wood. When the composition is used for plywood, it may be used in admixture with an adhesive of the phenolic or melamine type.

The composition of this invention can also include other wood preservatives or wood pesticides, such as cerosote oil, 8-hydroxyquinoline copper, copper naphthenate, chlordane, or dieldrin.

The amount of the active ingredient in the composition of this invention can be optional, but usually it is 0.01 to 70% by weight, preferably 0.1 to 50% by weight. If desired, the composition is diluted prior to use to a concentration of 0.5 to 1% by weight.

According to the present invention, there is also provided a method for preservation treatment of wood, which comprises treating wood or wood inhabited by wood-decaying microorganisms, with the compound of formula (I) in an amount effective for controlling the wood-decaying microorganisms.

The effective amount is optionally changed according, for example, to the type of wood, the purpose of use, and the treating conditions, but preferably, it is about 0.1 to about 5 Kg per m$^3$ of the wood to be treated. If desired, the compound of formula (I) can be used in a greater amount. Preferably, the treatment of wood is carried out such that the active compound not only adheres to the surface of the wood, but also pene-

Table 2

| | Lenzites trabea | | | Coniophora puteana | | | Lentinus lepideus | | | Poria monticola | | |
|---|---|---|---|---|---|---|---|---|---|---|---|---|
| | | | | | | 48 hours later | | | | | | |
| Compound No. 1 | 100 ppm | 50 ppm | 30 ppm | 100 ppm | 50 ppm | 30 ppm | 100 ppm | 50 ppm | 30 ppm | 100 ppm | 50 ppm | 30 ppm |
| | 100 | 100 | 100 | 100 | 100 | 100 | 100 | 100 | 100 | 100 | 100 | 100 |

Test Example 2

Test for fungicidal activity on wood chips:

A wood chip (cypress, 2 × 2 × 1 cm) was washed thoroughyl with warm water, dried, and placed in a highwalled Petri dish. The Petri dish was put in an autoclave to sterilize the wood chip at 120° C for 20 minutes. A 0.07% by weight acetone solution of each of the compounds shown in Table 3 was injected into the chip at reduced pressure, and the chip was dried in the air. The wood chip was then subjected ten times repeatedly to a weatherability-imparting treatment comprising washing it with water for 1 hour, drying it in the air for 23 hours, and heating it at 60° C for 24 hours.

Each of the wood chip so treated and another wood chip sample treated as above except the weatherability imparting treatment was placed on the colony of each of wood-decaying fungi (Coriolus versicolor and Tyromyces palustris) grown in a quartz sand culture medium (2% malt extract, 1% glucose, 0.5% peptone) and allowed to decay at 25° C for 3 months. The weight of each of the samples was measured, and the rate of weight loss (A) of the sample caused by decay and the rate of weight loss (B) of a sample not subjected to the wood-decaying fungi were measured. The anti-decay effect value of each of the samples was calculated on the basis of the following equation.

$$\text{Anti-decay effect value} = \frac{B - A}{B} \times 100$$

The results are shown in Table 3.

Table 3

| | Anti-decay effect value | | | |
|---|---|---|---|---|
| | No weatherability-imparting treatment | | After 10 cycles of the weatherability-imparting treatment | |
| Compound No. | Coriolus versicolor | Tyromyces palustris | Coriolus versicolor | Tyromyces palustris |
| 1 | 100 | 100 | 100 | 100 |
| 3 | 98 | 100 | 89 | 93 |
| 6 | 100 | 100 | 98 | 99 |
| 11 | 95 | 97 | 87 | 90 |

What we claim is:

1. A method for preservation treatment of wood which comprises treating wood or wood inhabited by wood-decaying microorganisms with 2H-benzopyran-2-spiro-3'-phthalide or its derivative of the following formula

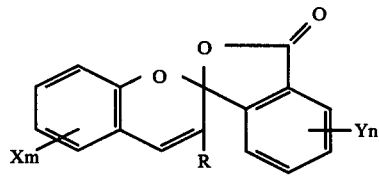

wherein each of X and Y is a member selected from the group consisting of halogen atoms, a nitro group, an amino group, alkyl groups, alkenyl groups, alkoxy groups, alkylthio groups and alkyl-substituted amino groups; m and n are an integer of 0 to 4, and when m is an integer of 2 to 4 and n is an integer of 2 to 4, a plurality of members X and Y may be identical or different; R is a member selected from the group consisting of a hydrogen atom, alkyl groups and a phenyl group; and each of X and Y may be positioned at two adjacent carbon atoms on the benzene ring and may form another benzene ring together with these carbon atoms, in an amount effective for controlling said wood-decaying microorganisms.

2. The method of claim 1 wherein the compound of formula (I) is used in an amount of about 0.1 to 5 Kg per m³ of the wood to be treated.

3. The method of claim 1 wherein in formula (I), each of X and Y is a member selected from the group consisting of halogen atoms, a nitro group, an amino group, alkyl groups containing 1 to 4 carbon atoms, alkenyl groups containing 2 to 4 carbon atoms, alkoxy groups containing 1 to 12 carbon atoms, alkylthio groups containing 1 to 12 carbon atoms and $C_1$–$C_6$ alkyl-substituted amino groups, and R is a member selected from the group consisting of a hydrogen atom, alkyl groups containing 1 to 4 carbon atoms and a phenyl group.

4. A method according to claim 1, wherein the 2—H—benzopyran-2-spiro-3'-phthalide compound is used in the form of a composition consisting essentially of said compound and a carrier or diluent.

5. A method according to claim 1, wherein the 2—H—benzopyran compound is present in an amount of 0.1 to 70%, based on the total weight of the composition.

* * * * *

UNITED STATES PATENT OFFICE
CERTIFICATE OF CORRECTION

Patent No. 4,075,121  Dated February 21, 1978

Inventor(s) KAZUHIKO KONNO et al.

It is certified that error appears in the above-identified patent and that said Letters Patent are hereby corrected as shown below:

Cover page, under [30] Foreign Application Priority Data, change "1976" to -- 1975 -- and change "51" to -- 50 --.

Signed and Sealed this

Twentieth Day of June 1978

[SEAL]

Attest:

RUTH C. MASON
Attesting Officer

DONALD W. BANNER
Commissioner of Patents and Trademarks